United States Patent
Fichtinger et al.

(10) Patent No.: US 9,743,912 B2
(45) Date of Patent: Aug. 29, 2017

(54) AUTOMATED INTRAOPERATIVE ULTRASOUND CALIBRATION

(71) Applicant: QUEEN'S UNIVERSITY AT KINGSTON, Kingston (CA)

(72) Inventors: Gabor Fichtinger, Kingston (CA); Purang Abolmaesumi, Vancouver (CA); Clif E. Burdette, Champaign, IL (US); Thomas Kuiran Chen, Burnaby (CA); Andras Lasso, Kingston (CA); Tamas Heffter, Kingston (CA)

(73) Assignee: QUEEN'S UNIVERSITY AT KINGSTON, Kingston, ON (CA)

( * ) Notice: Subject to any disclaimer, the term of this patent is extended or adjusted under 35 U.S.C. 154(b) by 100 days.

(21) Appl. No.: 14/068,990

(22) Filed: Oct. 31, 2013

(65) Prior Publication Data
US 2014/0121501 A1    May 1, 2014

Related U.S. Application Data

(60) Provisional application No. 61/720,779, filed on Oct. 31, 2012.

(51) Int. Cl.
*A61B 8/00* (2006.01)
*A61B 8/08* (2006.01)
(Continued)

(52) U.S. Cl.
CPC ............ *A61B 8/587* (2013.01); *A61B 8/0841* (2013.01); *A61B 8/12* (2013.01); *A61B 8/4209* (2013.01);
(Continued)

(58) Field of Classification Search
CPC ........ G01N 29/30; G01H 3/005; A61B 8/587; A61B 8/58; G09B 23/28
(Continued)

(56) References Cited

U.S. PATENT DOCUMENTS 5,196,343 A    3/1993 Zerhouni et al.
2001/0053870 A1*  12/2001 Loffler ................ A61N 5/1007
                                                       600/7
(Continued)

FOREIGN PATENT DOCUMENTS

EP    1095628 A2    5/2001
EP    1987764 A1   11/2008
(Continued)

OTHER PUBLICATIONS

Barratt, D.C., et al., "Self-calibrating 3D-ultrasound-based bone registration for minimally invasive orthopedic surgery," IEEE Trans. Med. Imaging, pp. 312-323, (2006).
(Continued)

*Primary Examiner* — Daniel S Larkin
*Assistant Examiner* — Anthony W Megna Fuentes

(57) ABSTRACT

An ultrasound calibration phantom comprises a portion including at least one fiducial structure having a selected geometric arrangement; a portion adapted for mechanical coupling of the ultrasound calibration phantom to a transrectal ultrasound (TRUS) stepper; and a guide for at least one surgical instrument, the guide being mechanically coupled to the fiducial structure and/or to the TRUS stepper at a selected pose relative to the fiducial structure. A calibration method uses the calibration phantom and provides automatic, intraoperative calibration of ultrasound imaging systems. The invention is useful in ultrasound-guided clinical procedures.

20 Claims, 14 Drawing Sheets

(51) Int. Cl.
A61N 5/10 (2006.01)
A61B 8/12 (2006.01)
A61B 17/00 (2006.01)
(52) U.S. Cl.
CPC .......... *A61N 5/1007* (2013.01); *A61N 5/1027* (2013.01); *A61B 8/4263* (2013.01); *A61B 8/4281* (2013.01); *A61B 2017/00274* (2013.01); *A61N 2005/1058* (2013.01)
(58) Field of Classification Search
USPC .................................. 73/1.86; 600/437–473
See application file for complete search history.

(56) References Cited

U.S. PATENT DOCUMENTS

| 2006/0241432 A1 | 10/2006 | Herline et al. | |
|---|---|---|---|
| 2007/0276234 A1* | 11/2007 | Shahidi | 600/437 |
| 2007/0291895 A1 | 12/2007 | Yin et al. | |
| 2008/0183075 A1 | 7/2008 | Govari et al. | |
| 2012/0059251 A1* | 3/2012 | Bakker | A61B 5/0062 600/424 |

FOREIGN PATENT DOCUMENTS

| GB | 2436424 A | 9/2007 |
|---|---|---|
| WO | 9960921 A1 | 12/1999 |
| WO | 0028554 A1 | 5/2000 |
| WO | 2004100761 A2 | 11/2004 |
| WO | 2005067800 A1 | 7/2005 |
| WO | 2007098899 A2 | 9/2007 |
| WO | 2008093080 A2 | 8/2008 |
| WO | 2008143998 A1 | 11/2008 |

OTHER PUBLICATIONS

Boctor, E.M., I. Iordachita, G. Fichtinger, and G.D. Hager, "Ultrasound self-calibration," Proceedings of SPIE Medical Imaging: Visualization, Image-Guided Procedures, and Display, edited by K. R. Cleary and R. L. Galloway, Jr. (SPIE, San Diego, CA, 2006), vol. 6141, pp. 61412NI-61412NI2.
Boctor, E.M., I. Iordachita, G. Fichtinger, and G.D. Hager, "Real-time quality control of tracked ultrasound," Leet. Notes Comput. Sci. 3749, 621-630 (2005).
Boctor, E.M., et al., "Rapid calibration method for registration and 3D tracking of ultrasound images using spatial localizer," Annual Conference of the International Society for Optical Engineering (SPIE) on Medical Imaging, Ultrasonic Imaging and Signal Processing, vol. 5035, p. 521-532.
Boctor, E.M. et al., "Bootstrapped Ultrasound Calibration," Stud. Health Technol. Inform. pp. 61-66, (2005) (Abstract only).
Chen, T.K., A.D. Thurston, RE. Ellis, and P. Abolmaesumi, "A real-time freehand ultrasound calibration system with automatic accuracy feedback and control," Ultrasound Med. Biol. 35(1), 79-93 (2009).
Goldstein, A., M. Yudelev, R.K. Sharma, and E. Arterbery, "Design of quality assurance for sonographic prostate brachytherapy needle guides," J. Ultrasound Med. 21, 947-954 (2002).
Khamene, A. et al., "A Novel Phantom-Less Spatial and Temporal Ultrasound Calibration Method," MICCAI, pp. 65-72 (2005).
Krupa, A., "Automatic Calibration of a Robotized 3D Ultrasound Imaging System by Visual Servoing," IEEE, pp. 4136-4141, (2008).
Masamune, K. et al., "System for Robotically Assisted Percutaneous Procedures with Computed Tomography Guidance," Computer Aided Surgery, vol. 6: 370-383, (2001).
Mercier, L., et al., "A review of calibration techniques for freehand 3-D ultrasound systems," Ultrasound Med. Biol. vol. 4 pp. 449-471 (2005).
Mutic, S., D.A. Low, G.H. Nussbaum, J.F. Williamson, and D. Haefuer, "A simple technique for alignment of perineal needle template to ultrasound image grid for permanent prostate implants," Med. Phys. 27, 141-143 (2000).
Ng, A., A. Beiki-Ardakan, S. Tong, D. Moseley, J. Siewerdsen, D. Jaffray, and I.W. T. Yeung, "A dual modality phantom for cone beam CT and ultrasound image fusion in prostate implant," Med. Phys. 35, 2062-2071 (2008).
Merrick G.S., et al., "Initial analysis of Pro-Qura: a multi-institutional database of prostate brachytherapy dosimetry," Brachyherapy, 6(1), 9-15 (2007).
Pfeiffer, et al., AAPM Task Group 128: Quality assurance tests for prostate brachytherapy ultrasound systems, Med. Phys., vol. 35(12), 5471-5489 (2008).
Viswanathan, A. et al., "Immediate Ultrasound Calibration from Two Poses and Minimal Image Processing," Seventh Annual Conference on Medical Image Computing and ComputerAssisted Intervention, MICCAI 2004, Proceedings in Lecture Notes in Computer Science, vol. 3217, pp. 446-454, Springer (2004).
Zelefsky, et al., "Five-year outcome of intraoperative conformal permanent I-125 interstitial implantation for patients with clinically localized prostate cancer," Int. J. Radiat Oncol Biol Phys, 67(1 ), 65-70 (2007).

* cited by examiner

AUTOMATED INTRAOPERATIVE ULTRASOUND CALIBRATION

FIELD

This invention relates generally to the field of ultrasound-guided clinical procedures. In particular, the invention relates to devices and methods for automatic, intraoperative calibration of ultrasound imaging systems. The devices and methods are useful in clinical procedures such as ultrasound-guided brachytherapy.

BACKGROUND

Prostate cancer is the second most frequently diagnosed cancer and the sixth leading cause of cancer death in men. Brachytherapy has emerged as a definitive treatment for early stage prostate cancer. The procedure entails permanent implantation of small radioactive isotope capsules (seeds) into the prostate to kill the cancer with radiation.

Prostate brachytherapy is delivered with real-time transrectal ultrasound (TRUS) image guidance (FIG. 1). Typically, the TRUS probe 2 is translated and rotated by a mechanical stepper 4 in the rectum 6 with its displacement and rotation angle tracked by encoders on the stepper. Individual TRUS images of prostate contours are then compounded into a volume based on which an implant plan can be created and a radiation dose calculated. Finally, under real-time, intraoperative TRUS image guidance, the actual implants are delivered to the prostate 8 transperineally by needles 10 inserted through a template 12 that contains a rectilinear grid of guide holes. Success of this treatment depends on an accurate plan of radiation dosimetry and a precise delivery of the implant.

The intrinsic accuracy of a brachytherapy system is solely determined by a unique procedure called "calibration", where a spatial registration between the coordinate systems of the TRUS and the template must be established prior to the implant procedure. Inaccurate system calibration causes faulty needle and radiation source placement, which may directly contribute to dosimetry errors, toxicity, and treatment morbidity.

In current practice, brachytherapy system calibration is a laborious, three-stage process:

Stage 1: An operator (typically a medical physicist) ascertains whether the TRUS image truthfully represents the size and shape of scanned objects and whether a series of individual images can be correctly stacked in space to reconstruct an accurate TRUS volume. For these purposes, artificial objects (phantoms) are employed with known geometry suspended in tissue-mimicking gel (to match the speed of sound in tissue). Phantoms are made commercially for these tasks; e.g., the industry-standard Brachytherapy Phantom CIRS 045 manufactured by Supertech, Elkhart, Ind. (U.S. Pat. No. 5,196,343). The operator scans the phantom, measures the distance, size, shape, and volume of the visible 2D and 3D features in the TRUS images, and then compares them to the known geometric specifications provided by the phantom manufacturer. Such measurements are conducted manually using rulers and calipers, either on the display of the ultrasound scanner, or on the printed TRUS images.

Stage 2: The operator calculates the relative spatial transformation between the coordinate frame of the TRUS images and the coordinate frame of the template. In the usual workflow, the operator mounts the template and the TRUS probe on a stand, dips the probe in a water tank, inserts needles through the template into the tank under TRUS imaging, marks the needle tips in the images, and calculates the transformation between the TRUS and template coordinate frames.

Stage 3: For some TRUS scanners that offer the ability to superimpose a square grid of coordinates on the real-time image, the overlaid grid lines must be aligned with the grids on the template. This is typically done by using eyesight and manually adjusting the scanner's setup. The user dips needles through the template into a water tank and then turns the knobs on the TRUS scanner until the grid lines appear to coincide with the artifacts created by the needles.

There are a number of technical elements in the calibration workflow that can lead to substantial bias and error in the final result:

The needles may be bent, therefore the segmented tip positions do not truthfully correspond to the physical locations of the template holes, which leads to erroneous template-TRUS registration;

The needle tip may be inaccurately segmented, especially when beveled implant needles are used;

The coordinates of the needle holes may be erroneously recorded;

The depth of the needle may be erroneously measured and recorded;

The number of needles used may be inappropriate; typically, too few needles are used;

The distribution of needle positions may be inappropriate, introducing bias if needle tips do not properly surround the location of the prostate;

The speed of sound in water is different from the speed of sound in human tissue, which can result in significant distance measurement errors in the TRUS image.

Overall, the procedure is laborious, more qualitative than quantitative, and involves a great deal of eyeballing and subjective judgments by the operator.

Furthermore, the calibration is performed only periodically (primarily due to the inefficiency of the procedure), mostly outside the operating room, with the assumption that calibration parameters remain valid over time. In reality, however, calibration parameters may change during storage, transportation and setup of the equipment.

Perhaps most critically, the system calibration errors are difficult to detect during the procedure so the brachytherapist has no assurance whether the system is functioning correctly in the operating room. There is no validation mechanism in the current procedure to verify and ascertain the calibration accuracy in the operating room.

Finally, brachytherapy calibration, with its current practice, is a major recurring cost for care facilities, consuming manpower, time and money. One must book a calibration room, decommit the TRUS unit from clinical use, transport the equipment, prepare supplies (needles, water tank, etc.), set up the system, collect and process data, and log, analyze and document the results, dispose all used supplies, pack away the brachytherapy system, and return the TRUS scanner to the clinic. This workflow needs to be repeated from time to time.

SUMMARY

Provided herein is an ultrasound calibration phantom, comprising: a portion including at least one fiducial structure having a selected geometric arrangement; a portion adapted for mechanical coupling of the ultrasound calibration phantom to a transrectal ultrasound (TRUS) stepper; and a guide for at least one surgical instrument, the guide being mechanically coupled to the fiducial structure and/or to the TRUS stepper at a selected pose relative to the fiducial structure.

In one embodiment, the portion including the at least one fiducial structure further includes an ultrasound coupling medium. In one embodiment, the calibration phantom further comprises a portion that interfaces with an ultrasound probe. The ultrasound probe may be a transrectal ultrasound (TRUS) probe.

In one embodiment, the at least one fiducial structure comprises a plurality of fiducial lines in a selected geometric arrangement. In one embodiment, the at least one fiducial structure comprises at least one Z-wire structure.

In one embodiment, the ultrasound calibration phantom comprises: a first fiducial structure having a selected geometric arrangement, the first fiducial structure corresponding to a transverse image plane; and a second fiducial structure having a selected geometric arrangement, the second fiducial structure corresponding to a sagittal image plane.

In one embodiment, the guide comprises a template. The template may be a brachytherapy template. In another embodiment the guide comprises a brachytherapy needle template. In another embodiment, the guide comprises a robot.

Also provided herein is a method for calibrating an ultrasound system, comprising: continuously acquiring ultrasound images from a calibration phantom as described herein while simultaneously tracking motion of an ultrasound probe; performing a temporal calibration to synchronize individual ultrasound image frames with their respective positions; segmenting the ultrasound images of the phantom to extract pixel locations of phantom geometry; subjecting the pixel locations of the segmented phantom geometry, together with their corresponding physical coordinates in the phantom, to a closed-form formula or an iterative solver to calculate calibration parameters; determining accuracy of a calibration result, measured as a reconstruction error against a known ground truth; and exporting a final calibration outcome.

In one embodiment, determining accuracy of a calibration result includes determining whether the calibration result is satisfactory. In another embodiment, determining accuracy of a calibration result includes updating and displaying reconstruction error in real time.

In one embodiment, the method includes exporting a final calibration outcome when the determining is completed or when the reconstruction error reaches an acceptable level In various embodiments, the method is used for real-time monitoring of ultrasound images during a clinical procedure. The clinical procedure may be a brachytherapy procedure, or a transrectal ultrasound (TRUS) brachytherapy procedure.

In one embodiment, the ultrasound system is a transrectal ultrasound (TRUS) system and the ultrasound probe is a TRUS probe.

BRIEF DESCRIPTION OF THE DRAWINGS

For a better understanding of the invention, and to show more clearly how it may be carried into effect, embodiments will be described, by way of example, with reference to the accompanying drawings, wherein.

DETAILED DESCRIPTION OF EMBODIMENTS

Figure 1:
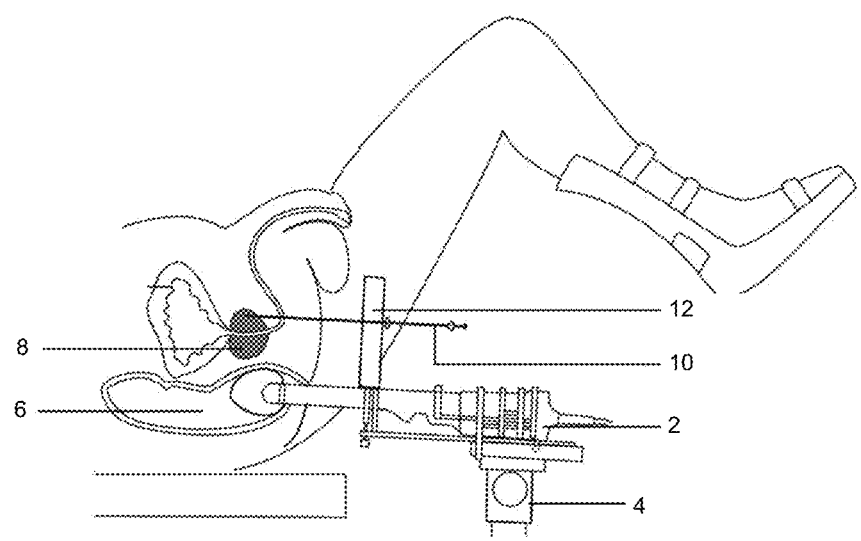
FIG. 1 is a diagram showing TRUS-guided prostate-cancer brachytherapy with needle inserted into the prostate through a template into a patient in the lithotomy position.

Described herein is an ultrasound calibration phantom and a fast, automatic method to calibrate an ultrasound system that provides substantially instant error feedback. The calibration phantom and method may be used in the operating room, i.e., intraoperatively. A calibration phantom as described herein mechanically couples a guide for at least one medical instrument with a fiducial at a selected pose relative to the fiducial. Real-time ultrasound images are acquired from the calibration phantom and processed by the calibration system, and a coordinate transformation between the guide and the ultrasound images is computed automatically. That is, the surgical instrument space provided by the guide is registered with the ultrasound image space. The system substantially instantly generates a report of the target reconstruction accuracy based on the calibration outcome. Embodiments described herein provide automatic, intraoperative calibration of ultrasound that achieves high accuracy, precision, and robustness.

The ultrasound system may be a transrectal ultrasound (TRUS) system. However, it will be appreciated that the invention is not limited thereto. In one embodiment mechanical coupling is achieved by attaching the calibration phantom and the guide to a TRUS stepper. In other embodiments mechanical coupling is achieved by attaching the calibration phantom to the guide, e.g., as a unibody structure. In one embodiment the guide is a template, such as, for example, a needle template, used in procedures such as brachytherapy. In another embodiment the guide is a robot.

Embodiments are described primarily with respect to TRUS in prostate cancer brachytherapy; however, it will be appreciated that the invention is not limited thereto. For example, the embodiments may be applied to other forms of transperineal interventions, including but not limited to localized therapies (thermal ablation, cryo ablation, injections, etc.) and biopsies. It is furthermore appreciated that embodiments for use with TRUS may be applied not only to prostate cancer brachytherapy, but to any procedure where TRUS is used, such as, for example, gynecological procedures.

TRUS calibration is implicitly present in a brachytherapy procedure, and accordingly little work has been dedicated to this problem. In the context of tracked freehand ultrasound (US) imaging, however, many calibration technologies have been explored. Tracking is typically achieved by rigidly affixing the US probe with a localizer traced by a position sensing system. Calibration is typically conducted by scanning an artificial object (i.e., a phantom) with a fiducial of known (i.e., selected) geometric arrangement. For example, the selected geometric arrangement may be a cross-wire, three-wire, V-wire, or Z-wire (also referred to as N-wire) arrangement. Other geometric arrangements may also be used. Regardless of the geometric arrangement, the method includes identifying features in both the acquired images and the physical phantom space (which is known by construction). With both the position of the transducer and the phantom tracked by a localization system, an equation can then be built to convert between these two coordinate systems.

To solve for the calibration parameters, a general approach is to employ least-mean squares to minimize the distance between the features of interest in the image space and the phantom space. In some embodiments it may be advantageous to use robust least-mean squares method, which can automatically detect and ignore outliers (e.g., erroneously acquired or processed data). If an exact correspondence of the features between the two spaces can be established, a closed form solution is generally preferred. If, on the other hand, the precise location of features in the phantom space is unknown (which is the case for some phantom designs), then a method based on iterative regression may be used. Iterative approaches have the advantage of greater flexibility in constraining the transform (e.g., iterative approaches can be used the same way with rigid, similarity, affine, etc. transforms; while a closed form method may only be used with a specific transform type), and allow a wider choice in the error metric (e.g., iterative methods can minimize the error measured for all the fiducial lines, in any coordinate space; while closed form methods may be limited to minimizing the error for certain fiducial lines, in specific three-dimensional coordinate space only). Iterative approaches are, in general, less robust than closed-form solutions because of nonguaranteed convergence, potential trapping in local minima, and being sensitive to initial estimates. Also, to achieve adequate accuracy, iterative methods typically need more input data and computational time than closed-form techniques. For instance, calibration with a Cambridge phantom would require at least 550 images to achieve acceptable accuracy, as compared to around 6-30 images with a typical N-wire phantom. On the other hand, closed-form solutions face the challenge to automatically and accurately extract point-targets from an ultrasound image and are therefore typically conducted manually, which is undesirable in the operating room. Though the majority of the point-based calibration technologies are manual and laborious, there have been successful attempts to automate segmentation of images acquired from N-wire phantoms. For best results, an initial result computed by a closed-form solution may be further enhanced by an iterative solution. The chance of the iterative solution trapping in local minima is minimized, because the initial result is close to the global optimum.

It is desirable to have automatic, real-time feedback of calibration accuracy in the operating room. Boctor et al. (2005, 2006) proposed a real-time in vivo quality control mechanism that monitored the consistency in calibration parameters through frequent recalibration in the background. However, their validation on the calibration results was based on precision and not accuracy. It is important to note that a measure of precision is different from that of accuracy: precision defines the repeatability and consistency of the system, while accuracy evaluates how much the output is away from a known "ground truth" (typically measured independently). Not relying on a ground truth, a high precision (a low variance in results) does not necessarily guarantee a high accuracy. For example, it is possible that a calibration system that achieves highly consistent results may include a systematic error that renders the system inaccurate.

Embodiments provided herein remove or avoid the aforementioned problems by performing calibration tasks (i.e., Stage 2 and Stage 3 described above) at substantially the same time. Embodiments provide fast, automated, pure-computation based, intraoperative calibration, which may advantageously be used in the operating room when a patient is being prepared for surgery. Certain embodiments may be particularly well-suited for brachytherapy procedures, such as prostate cancer brachytherapy. As described herein, the current practice of preoperatively performed, labor-intensive, and subjective calibration processes is avoided. A calibration method as described herein may simultaneously reduce treatment costs, increase safety, and improve accuracy in applications such as, but not limited to, prostate cancer brachytherapy procedures.

Calibration Device

As described above, a calibration phantom provided herein mechanically couples the phantom and a surgical instrument guide. Preferably the phantom is precision-engineered. The phantom includes a fiducial of a design such as, for example, N-wire (also referred to as Z-fiducial). However, other designs may be used, such as cross-wire, three-wire, or V-wire. The phantom and the guide are combined as one member, e.g., in a "unibody" design, having geometric precision and structural integrity. The guide is coupled to the calibration phantom at a selected pose, such that the relative pose between the guide and the phantom, and hence the fiducial geometry, is known.

Figure 2A:
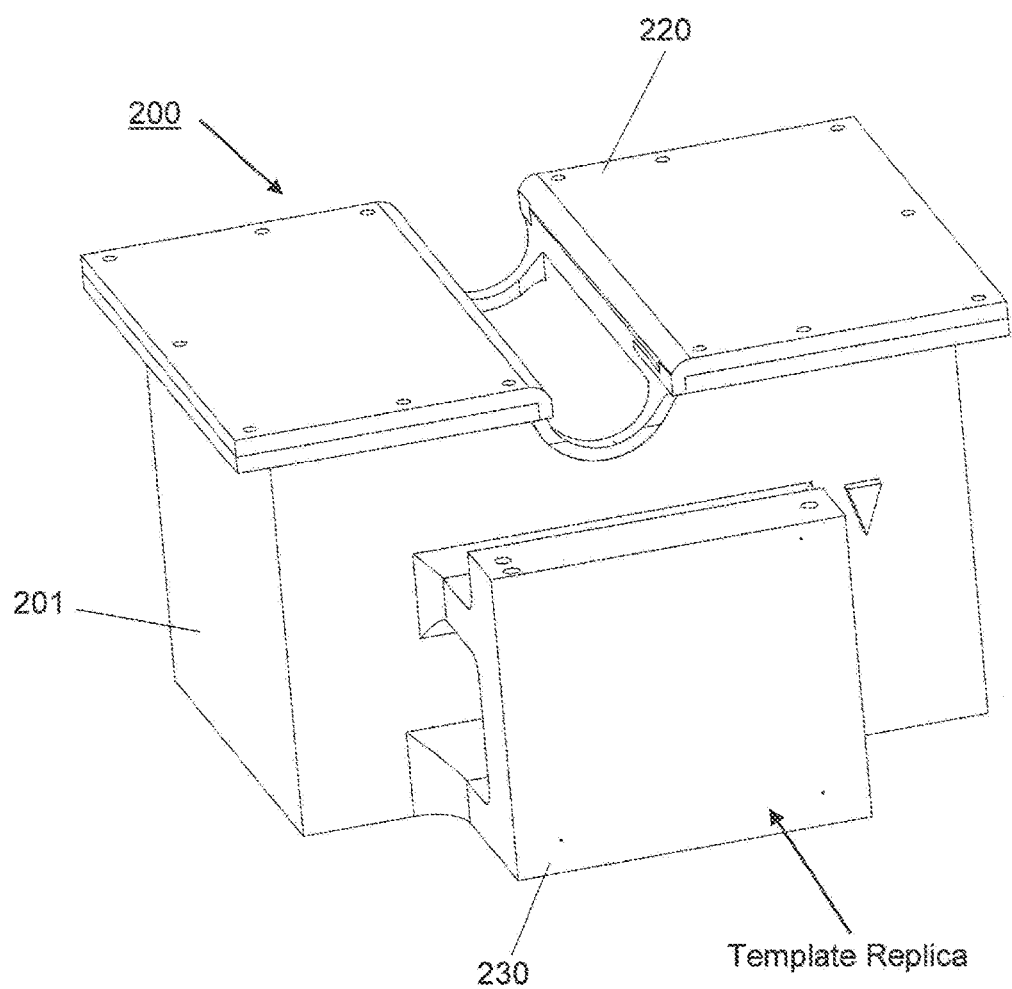
FIG. 2(a)-(d) shows a calibration phantom according to one embodiment wherein (a) is a CAD drawing of a complete assembly and (b)-(d) are photographs showing a complete assembly, inner N-wires, and a seal for a TRUS probe, respectively.

The calibration phantom may be designed using CAD software (FIG. 2(a)) and the CAD model may be exported to a 3-D printer to manufacture the parts. A production-grade, high-density, high-strength, and liquid-proof thermoplastic may be used to prepare the parts. An assembled embodiment 200 is shown in FIGS. 2(b)-(d).

Figure 2B:
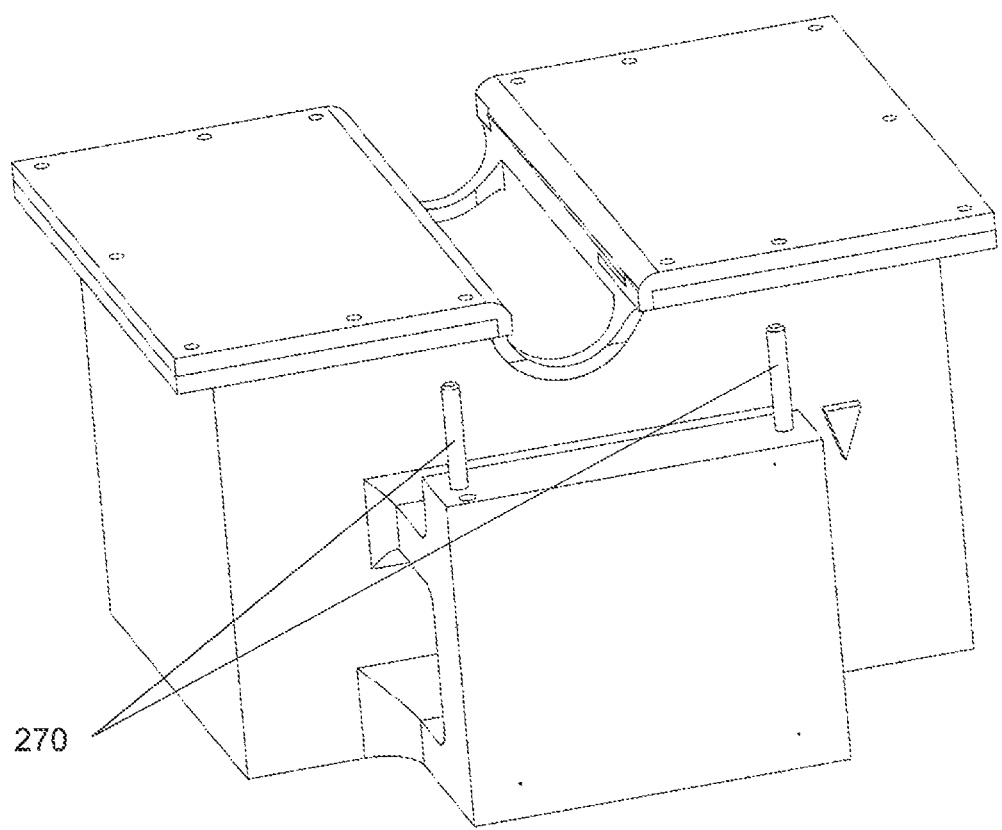

For example, in one embodiment the phantom includes three individual parts (FIG. 2(b)): a container box 201, an inner N-wire mount 210, and a sealing cover 220. The container box 201 houses the guide 230. The type of guide used will be determined by the intended clinical procedure. For example, the guide may be a brachytherapy needle template. The template may be a replica of an actual brachytherapy template, as shown in the embodiment of FIG. 2(a). Suitable mounting/alignment holes and/or hardware are provided on the calibration phantom for proper mounting to the stepper, such as posts 270 (see FIG. 2(b)) and corresponding holes. The container box may optionally contain an ultrasound coupling medium, which conveniently allows for calibration without submerging the phantom in water.

In some embodiments the phantom may be calibrated in water. To approximate the speed of sound in tissue (e.g., 1540 m/s), the container box may be filled with distilled water heated to a temperature of about 37° C. Alternatively, an additive such as salt may be added to the water. Preferably, an acoustic coupling medium is used to more closely match the speed of sound in tissue.

Figure 2C:
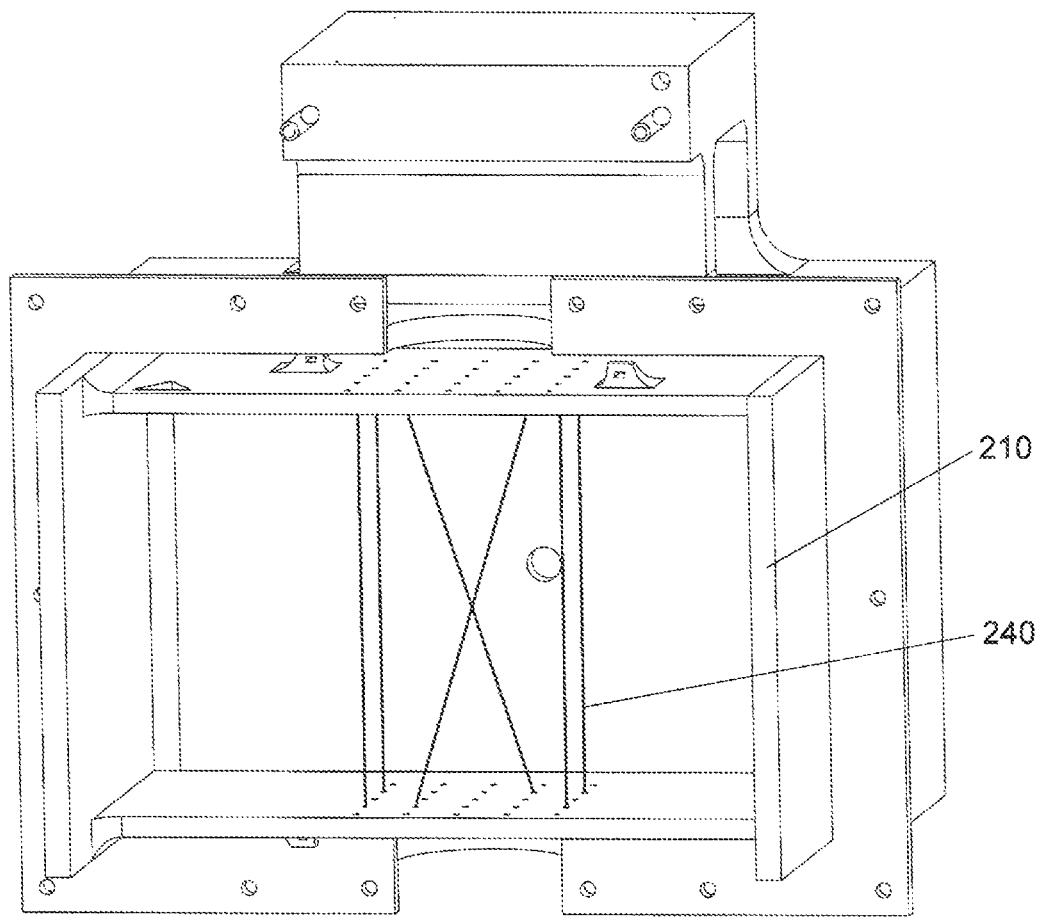
Figure 2D:
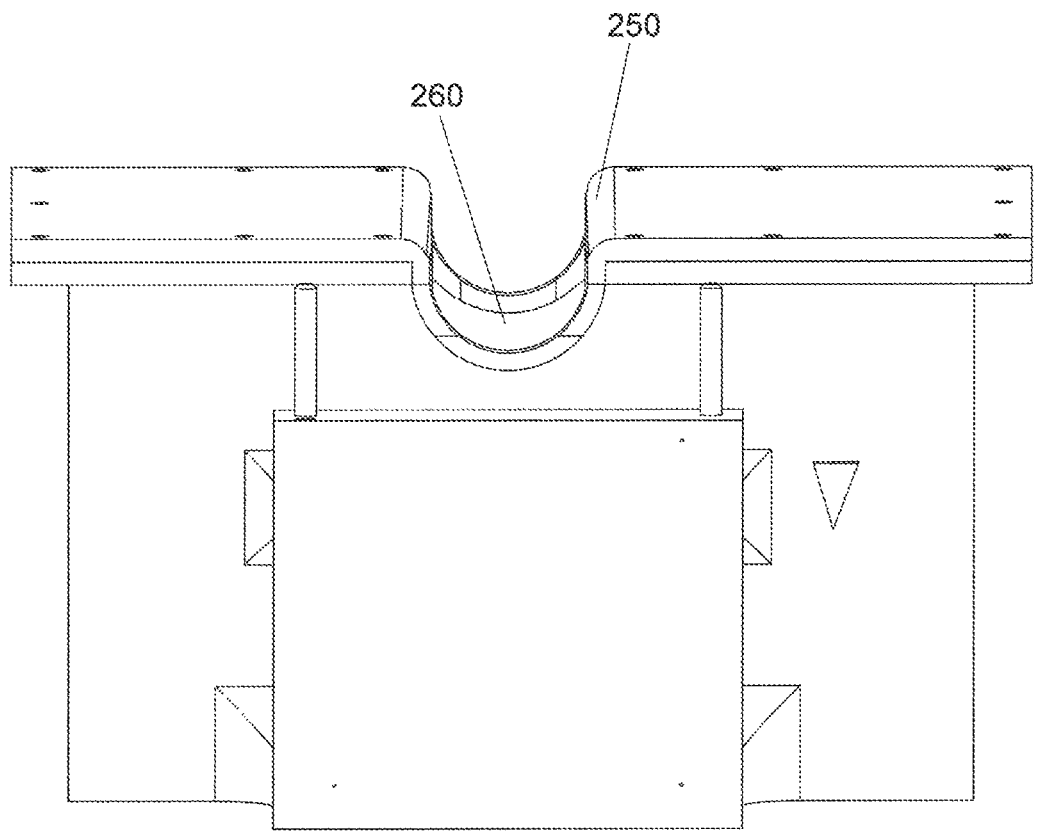

The inner N-wire mount 210 is optionally replaceable and fits snugly in the container box, as shown in FIG. 2(c). In one embodiment it consists of a front and a back plate connected by two side walls, forming a simple open-ended box. Holes may be provided on both the front and back plate to mount the N-wires 240. In embodiments for sagittal plane calibration, holes may also be provided on the sides to accommodate the associated set of N-wires (see below and FIG. 3). The N-wires may be made of nylon or other suitable material. The wires are of a diameter comparable to the wavelength of the ultrasound used. For example, the wires may be 0.4 mm in diameter, a size comparable to the TRUS wavelength used for prostate imaging (ranging typically from 0.2 to 0.5 mm), which would optimize the image appearance of the wires. The location of the N-wires encompasses the targeted area of the tissue under investigation in a clinical procedure (e.g., the prostate), thus maximizing the calibration accuracy.

In the embodiment shown in FIG. 2(d), the calibration phantom includes a portion 250 that interfaces with the ultrasound (e.g., TRUS) probe, and a membrane window 260 for ultrasound imaging. Typically such an embodiment would include an ultrasound coupling medium. The imaging window is on the posterior (bottom) side of the phantom, as shown in FIG. 2(d). For example, the membrane may be 0.8 mm thick, natural rubber. Natural rubber has an acoustic impedance (1.81 Mrayls) similar to that of water (1.48 Mrayls), allowing sound transmission in and out of the container with only small attenuation. In embodiments that do not include an ultrasound coupling medium, such as may be calibrated in water, the portion that accepts an ultrasound probe may be omitted.

In one embodiment the guide is a replica of all or a portion of a surgical instrument template, such as, for example, a brachytherapy template. For example, the guide may be a substantially exact replicate of the template/stepper interface (i.e., the guide corresponds to the size and distance of alignment hardware (e.g., rods, posts, holes, etc.) that connect a needle guidance template to a TRUS stepper). For example, for prostate brachytherapy, template model D1-1784RA (Burdette Medical Systems, Inc., Champaign, Ill.) which measures 81.0×71.1×19.1 mm and has a matrix of 13×13 holes at 5-mm spacing vertically and horizontally, may be used.

Figure 2E:
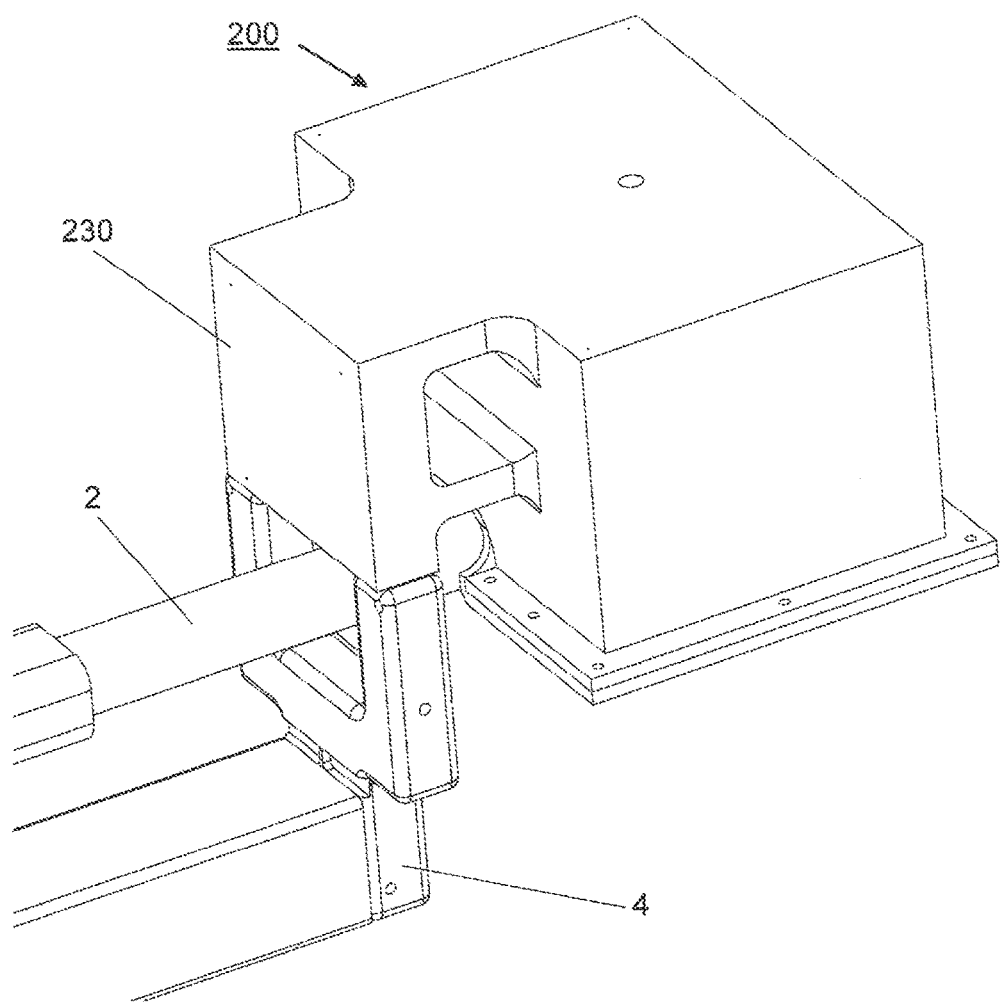
FIG. 2(e) is photograph showing a calibration phantom together with a TRUS probe mounted on a TRUS stepper, according to one embodiment.

For TRUS brachytherapy applications, the coupled phantom and template is mounted over the TRUS probe 2 on a brachytherapy stepper 4, using the standard mounting posts and holes provided for the template, as shown in FIG. 2(e), such that the entire assembly behaves substantially as a unibody structure. The TRUS probe makes contact with the membrane window of the calibration phantom (as in the case embodiment of FIG. 2(d), for example), where the probe can be translated and/or rotated to acquire TRUS images from the interior of the phantom.

Benefits of the unibody design of the calibration device, in which the phantom and the template are mechanically coupled, include: The design preempts the sterilization issues of the phantom, because it would be otherwise impractical to attach the phantom to the template which needs to be sterilized in the operating room. Also, precision coupling with a known relative pose between the phantom and the template ensures a very high accuracy and precision in localizing the phantom geometry during the calibration process.

Whereas Ng et al. (2008) proposed combining a phantom and template for registration of TRUS and cone-beam CT, certain features required for brachytherapy calibration were lacking. For example, the approach did not include knowing the relative pose between the template and phantom. Without this information, calibration between the template and ultrasound image is mathematically impossible to perform. Also, the specific arrangement of the wire structure in the phantom did not allow for computational determination of the wire positions in the ultrasound image. As a result, the wire positions can only be extracted manually. Manual extraction of wire positions in ultrasound involves a great deal of manual labor, subjective judgment, and "eyeballing", which ultimately lead to inconsistent results.

In contrast, a calibration phantom as described herein provides the phantom and the template in a unibody structure, wherein the relative pose between the fiducial and the template is known by design and established by precise machining. This allows calibration between the template and the ultrasound image to be performed. Furthermore, embodiments provided herein use phantoms with fiducial (e.g., wire) arrangements that are selected so as to be amenable to automatic and computational identification in the ultrasound images.

Figure 3:
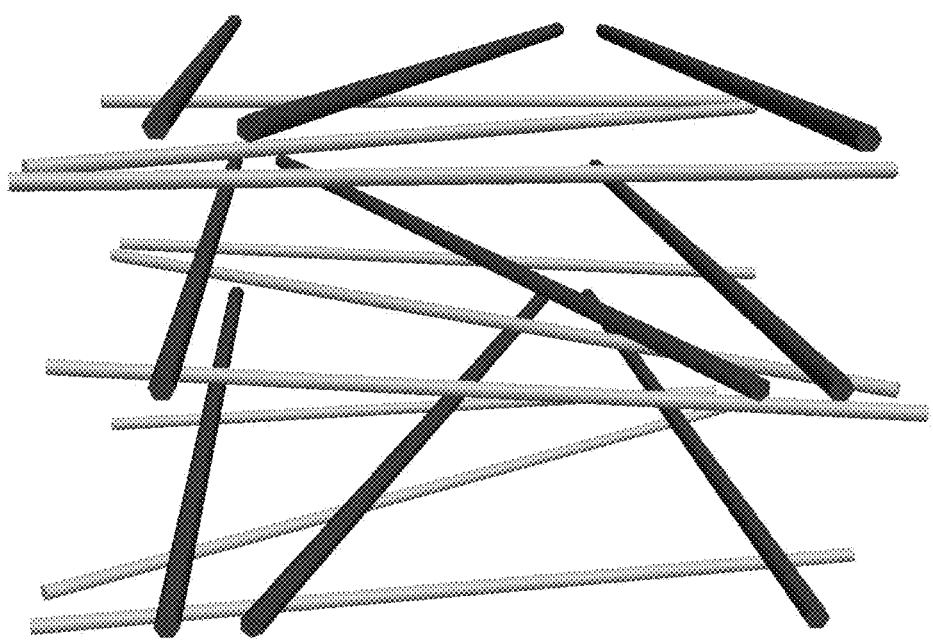
FIG. 3 is a diagram showing an arrangement of N-wires for transverse and sagittal image plane detection.

An ultrasound probe may contain two ultrasound transducers in different orientations. For example, a TRUS probe may include a first transducer for a transverse image plane that is orthogonal to the transducer's long axis, and a second transducer for a sagittal image plane that is parallel to the transducer's long axis. Embodiments have been described above with respect to one image plane (the transverse image plane). However, embodiments are also provided for the sagital image plane, either alone or in combination with the transverse image plane. A calibration phantom as described herein may be used to calibrate transducers having a transducer for a sagittal image plane by adding fiducials (e.g., N-wires) for that transducer. Various embodiments include a separate calibration phantom provided for each transducer, the same phantom mounted in two different orientations to the probe, or all the fiducials are included in one calibration phantom. The last option is feasible, because although all the fiducials are visible in both the transverse and sagittal images, the calibration method automatically detects which wires to use for the calibration of a particular transducer. As one example, to calibrate a probe with two such transducers, three N-wires may be added for each transducer, slightly translated and rotated by about 90 degrees. FIG. 3 shows such an embodiment, wherein two sets of three N-wires are shown in different shading.

By extending automated calibration to the sagittal image plane, both the transverse image and the sagittal image produced by the ultrasound probe can be co-registered and can be used for needle guidance or can be compounded together to produce a more accurate TRUS volume.

Calibration

Figure 4:
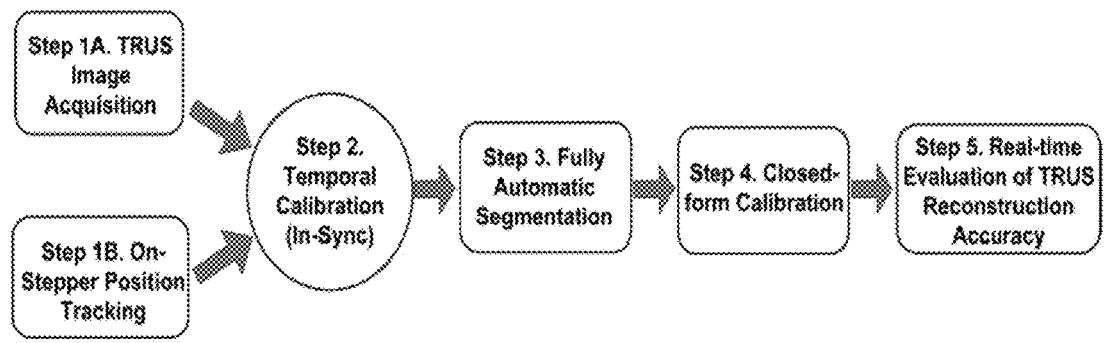
FIG. 4 is a flowchart showing a calibration procedure according to one embodiment.

FIG. 4 shows an embodiment of a calibration workflow, including five steps:

Step 1A. As input, TRUS images are continuously acquired from the phantom.

Step 1B. The motion (translation and/or rotation) of the TRUS probe is tracked by the brachytherapy stepper.

Step 2. A temporal calibration process is performed to synchronize individual TRUS image frames with their respective positions.

Step 3. TRUS images of the phantom are automatically segmented to extract the pixel locations of the phantom geometry.

Step 4. The pixel locations of the segmented phantom features, together with their corresponding physical coordinates collected in the phantom space, are fed to a closed-form formula to calculate the calibration parameters.

Step 5. Measured by a reconstruction error against a known ground truth, the accuracy of the calibration result may be fed back to the control loop to determine whether or not it is satisfactory. The reconstruction accuracy is updated, monitored and displayed in real time. Once the process converges or the reconstruction error reaches an acceptable level, the procedure is terminated and the final calibration outcomes exported. Alternatively, the calibration procedure can be performed using a fixed number of frames and/or requiring coverage of a specified translation and rotation range.

Compared to conventional manual brachytherapy calibration (i.e., Stages 2 and 3 described above), calibration as described herein accomplishes all the required tasks in one automated loop. First, the calibration outcome contains the homogenous spatial transformation parameters that register the TRUS image plane to the template. This accomplishes Stage 2 of the conventional calibration.

Second, as a byproduct of the calibration results, the calibration overlays the location of the template grid onto the transverse TRUS image, and in real time updates and displays a virtual grid through an interactive graphics interface to the user whenever the probe is being translated and/or rotated. This accomplishes Stage 3 of conventional calibration (as described above).

Embodiments will be further described by way of the following non-limiting examples.

EXAMPLE 1

Image acquisition, tracking, and temporal calibration in respect of TRUS prostate brachytherapy, using embodiments of the calibration device and method described above, will now be described.

1. Analogue Data Acquisition.

TRUS images were transferred from an analogue data output (e.g., S-video or composite port) of a TRUS scanner to an ImageSource DFG/USB2-LT USB framegrabber (Imaging Source, LLC., Charlotte, N.C.) installed in the host computer at 30 frames per second (fps). A benefit of using the analogue data is that it is the most common interface available on a standard TRUS machine, therefore provides the best hardware compatibility for the calibration to work with virtually any currently available TRUS scanners. A drawback is the relatively lower image quality compared to digital format. Because the ultrasound machine processes and stores all scan-converted image data digitally in its internal memory, a digital-to-analog (D/A) conversion of the data needs to be performed when outputting the signals to the analog video port, which is then converted back to digital by the USB video-capturing device on the host computer. This double conversion results in a degradation in image quality of the original, digital image. Analogue data acquisition was tested with five commercially available TRUS scanners:

Leopard 2001 (BK-Medical Systems, Inc., Peabody, Mass.)
Sonix MDP 4.0 Analogue Output (Ultrasonix Medical Corp., Richmond, BC, Canada)
Sonix TOUCH Analogue Output (Ultrasonix Medical Corp.)
VLCUS (Carolina Medical Systems, Inc.)
Terason 2000 (Teratech Corp., Burlington, Mass.).

2. Digital Data Acquisition.

For better imaging quality, higher data acquisition speed, and research purposes, some TRUS scanners offer a digital interface to acquire images directly from the internal image memory of the ultrasound machine. Accordingly, in one embodiment, digital data acquisition is included in the calibration method. Digital data acquisition may be based on, for example, through Ulterius or Porta interface (Ultrasonix Medical Corp.). The acquired imaging data can be B-mode or RF-mode, before or after scan conversion. Digital data acquisition was tested on Ultrasonix SonixMDP and SonixTOUCH scanners.

3. Stepper Position Tracking

While the TRUS images were being continuously acquired from the calibration device, the motion of the TRUS probe was simultaneously tracked by the brachytherapy stepper. Typically, there are two separate optical encoders to independently track the motion of the TRUS probe in real time: a translation encoder that reads the displacement of the probe along its long axis, and a rotation encoder that reads the rotation of the probe transversely. This position data was sent to the host computer via a serial-port connection to be associated with the image data. Calibration was tested with two brachytherapy stepper systems that are currently available:

Target Guide Stepper (Burdette Medical Systems, Inc., Champaign, Ill.)
Accuseed DS300 Stepper (Computerized Medical Systems, Inc., Saint Louis, Mo.).

4. Temporal Calibration

Since the images and the tracked probe positions are generated by separate hardware (the TRUS scanner and the stepper tracking system), proper synchronization between the two must be established to correctly associate each acquired TRUS image with its corresponding positional data. This process is referred to as "temporal calibration".

When a TRUS image is acquired and its corresponding stepper position recorded, both data can be time-stamped. However, the time-stamping process itself introduces some delay, because of the difference in processing speed between the ultrasound machine and the stepper system, as well as the necessary time required for data transfer (from the ultrasound machine and the stepper system to the host computer). The goal of temporal calibration is to determine this delay ("latency"). Temporal calibration is typically conducted by introducing some form of abrupt change in the motion of the ultrasound transducer that would also result in a traceable difference in the ultrasound image. The goal is to identify and match this difference in both the positional data and in the ultrasound image, based on which latency between the tracking and image acquisition is then computed. Alternatively, temporal calibration may be performed by computing the time offset that maximizes correlation between the position signal extracted from the images and the stepper. For the correlation-based method the probe has to be moved in a continuous, periodic pattern (e.g., translating the probe back and forth several times).

Figure 5:
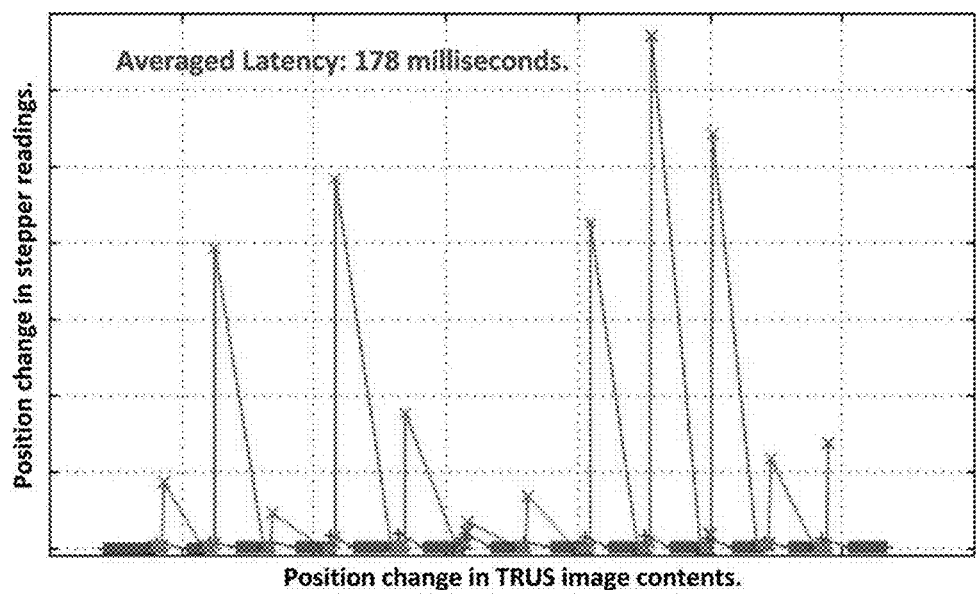
FIG. 5 is a plot showing an example of automated temporal calibration according to one embodiment.

The calibration method provides fast and automated temporal-calibration. One embodiment includes repeatedly and rapidly pausing and translating the TRUS probe on the stepper (e.g., every two seconds) while imaging the calibration phantom. FIG. 5 shows an example of the results of the temporal calibration. The abrupt and repeated motion caused positional changes in both the TRUS image contents and the stepper readings, which were automatically detected and registered together to compute the temporal latency.

5. Automated Segmentation

Calibration embodiments include an algorithm that automatically segments images acquired from the calibration phantom. The algorithm requires no user input during the calibration process. The typical cross-section view of a wire is a single small dot in the TRUS image, which is challenging for automatic segmentation for point-based calibration techniques. A major difficulty is how to accurately and robustly recognize the point targets in the presence of speckle, which has similar image intensities and shapes. To overcome this, the algorithm exploits unique features of fiducial. For example, two unique geometric features of N-fiducials in the image were used to assist the segmentation: the three collinear dots that form an N-wire intersection with the TRUS image plane, and the two nearly parallel lines that pass through these two layers of dots.

In one embodiment the segmentation algorithm includes four stages with various image processing techniques. First, dominant speckles are removed by a series of morphological operations. Pixels are then clustered to yield possible candidates of dots. Then the algorithm searches for lines composed of three dots, and further narrows the search space to multiple such lines close to being parallel. This four-stage algorithm works effectively with noisy input data with speckles, reflections and other typical ultrasound artifacts. For more technical details of the automated segmentation algorithm, please refer to Chen et al. (2009). For other fiducial designs, other unique features may similarly be exploited.

6. The Closed-form Calibration Method

Ultrasound probe calibration identifies features in both the acquired images and in the physical phantom space (which is known). With both the position of the transducer and the phantom tracked by a localization system, an equation can then be built to transform between these two coordinate systems.

Figure 6:
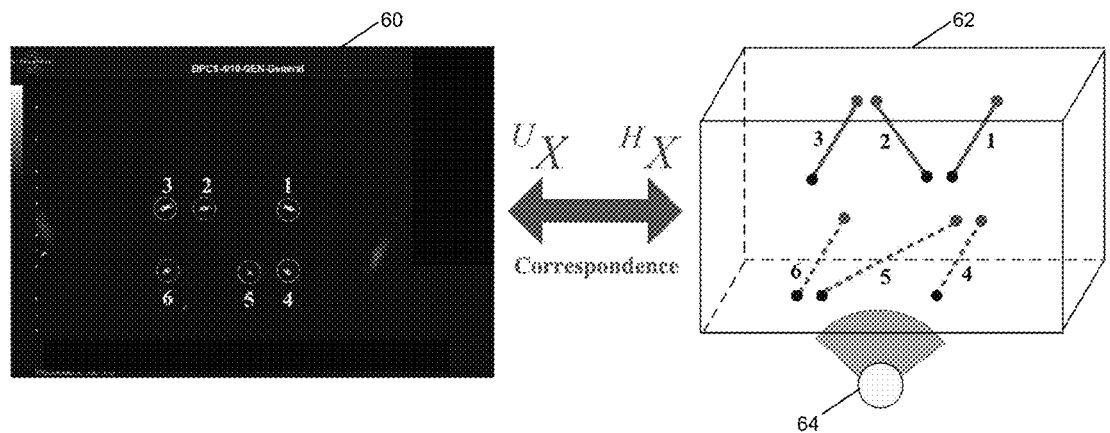
FIG. 6 shows a TRUS image of a calibration phantom and its correspondence to a unique N-wire geometry of a calibration phantom, according to one embodiment.

FIG. 6 shows a graphical representation 62 of the N-wire geometry of the calibration phantom used in this example, and the corresponding TRUS image 60 from a TRUS transverse probe 64. From this geometry the calibration parameters may be solved in a single closed-form equation. In the general case, let $^AX$ and $^BX$ denote 3D positions X expressed in coordinate frames A and B, respectively. $_A^BT$ then represents a homogeneous transformation that maps $^AX$ to $^BX$, as expressed by the generic equation:

$$^BX = {_A^BT} \, ^AX \qquad (1)$$

Figure 7:
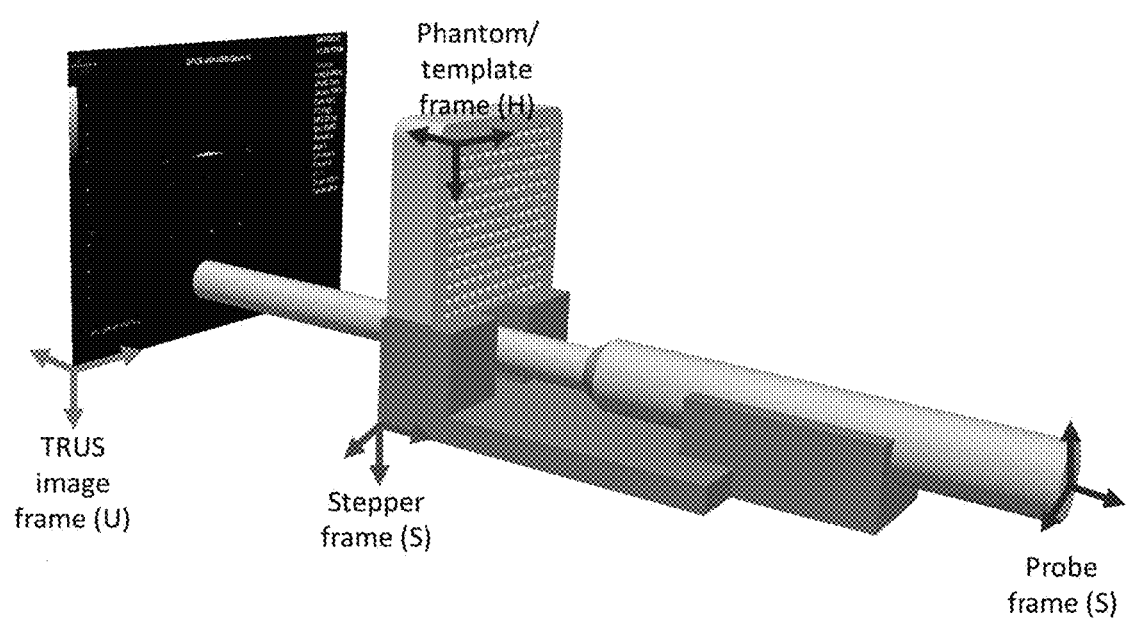
FIG. 7 is a diagram showing coordinate transformations from a template to a TRUS image.

In the present case, the objective of the calibration is to determine $_U^PT$, the transformation that brings a position from the TRUS image frame (U) to the TRUS probe frame (P) through a series of 3D spatial frame transformations as depicted by FIG. 7. Note that $_U^PT$ is a 4×4 matrix that encodes 8 calibration parameters (3 rotation parameters, 2 scaling factors, and 3 translation parameters) in a single homogeneous transformation.

To start, a set of TRUS images is acquired from the calibration phantom. The intersection point of a wire and the TRUS image plane is displayed as a gray-intensity dot in the image, which may be expressed in the TRUS image frame (U) and in the phantom frame (H) as $^UX$ and $^HX$, respectively (FIG. 6):

$$^UX = (_U^PT)^{-1} \cdot {_S^PT} \cdot {_H^ST} \, ^HX \qquad (2)$$

On the left side of Eq. (2), $^UX$ may be measured as the N-wire positions in the TRUS image frame. On the right side, $_S^PT$, the transformation from the stepper frame to the TRUS probe frame, is known from the stepper's position tracking of the probe. $_H^ST$, the transformation from the phantom frame to the stepper frame, was known by the calibration phantom design that mechanically couples the phantom geometry with the replica of the template affixed onto the stepper. $^HX$ is the corresponding physical position of $^UX$ in the phantom frame and can be calculated using the similar triangle geometry of the N-wires. Finally, $_U^PT$ is the unknown calibration parameter which is to be solved.

Both $^UX$ and $^HX$ can be expressed as 4×1 column vectors in homogeneous format, i.e., $^UX = [^Ux \; ^Uy \; 0 \; 1]'$ and $^HX = [^Hx \; ^Hy \; ^Hz \; 1]'$. For a number of m such N-fiducials, we can construct $^UX$ and $^HX$ in matrices as:

$$U_X = \begin{pmatrix} U_{x_1} & U_{x_2} & \cdots & U_{x_m} \\ U_{y_1} & U_{y_2} & \cdots & U_{y_m} \\ 0 & 0 & \cdots & 0 \\ 1 & 1 & \cdots & 1 \end{pmatrix} \qquad (3)$$

$$H_X = \begin{pmatrix} H_{x_1} & H_{x_2} & \cdots & H_{x_m} \\ H_{y_1} & H_{y_2} & \cdots & H_{y_m} \\ H_{z_1} & H_{z_2} & \cdots & H_{y_m} \\ 1 & 1 & \cdots & 1 \end{pmatrix}.$$

Note the difference in the 3rd rows between matrices of $^UX$ and $^HX$. Points in the TRUS image frame do not have a z-coordinate, so without losing generality all zeros are used for their 3rd components.

In all, Eqs. (2) and (3) establish an over-determined system for $_U^PT$, which can be solved using a straightforward implementation of linear least squares. For N-wire-based calibration technologies, a minimum number of data points (e.g., m=120) is necessary for high-accuracy calibration.

7. The Iterative Calibration Method

After the closed-form calibration method has been completed, an iterative method can be applied to further enhance the results. The result of the closed-form step is used as an initial value for the iterative solution. A standard non-linear optimizer, such as the Levenberg-Marquardt algorithm can be used for finding the final transform, that minimizes the error. The transform can have 7 or 8 degrees of freedom: 3 rotations, 3 translations and 1 or 2 scaling. One scaling parameter is used if the horizontal and vertical spacing is assumed to be the same. Two scaling parameters are used if the horizontal and vertical image spacing is to be determined separately, e.g., for estimating differences in actual and assumed speed-of-sound in the coupling medium. The error metric can be the same as the one used in the closed-form solution. Alternatively, the error metric can be the mean or root mean square error computed from the difference between the computed and actual observed positions of the fiducials in the image.

8. Real-Time Evaluation of Calibration Accuracy

To evaluate the calibration accuracy, the calibration phantom was scanned and the cross-sections of four sets of parallel wires (#1, #3, #4, and #6 in FIG. 6) were reconstructed into the 3D world coordinate system using the computed calibration parameters. These were compared, respectively, to their known physical locations (the gold standard) to compute a mean residual reconstruction error, defined as the line reconstruction error (LRE):

$$\|LRE\|=\|{}^H X - {}_S^H T \cdot {}_P^S T \cdot {}_U^P T \cdot {}^U X\| \qquad (4)$$

where ${}_U^P T$ is the calibration outcome to evaluate, ${}_P^S T$ is the transformation from the TRUS probe frame to the stepper frame given by the stepper's position readings, ${}_S^H T$ is the transformation from the stepper frame to the calibration phantom frame that is known by the phantom geometry mechanically coupled to the stepper system, ${}^U X$ is the identified position of the wire in a TRUS image, and ${}^H X$ is the corresponding wire location known by the calibration phantom design (as the ground truth).

There are several important facts to note about the calibration accuracy evaluation. First, LRE is an absolute Euclidean distance between a reconstructed point and the respective wire (i.e., a point-line distance) in space, so it remains invariant to frame transformations, and has units of millimeters.

Second, the calibration performs this error measurement in real time by automatically extracting the wire positions and reconstructing them in the physical phantom space using the computed calibration parameters.

Further, because the same phantom geometry is utilized for both calibration and accuracy evaluation, the data used for LRE calculation may be separated from those used for calibration to avoid a systematic bias in the error evaluation toward the calibration results.

Finally, a significant advantage of this automatic error retrieval is that the process can be performed quickly and efficiently for an extensive data set collected from a variety of experimental conditions to thoroughly evaluate calibration quality. This has enabled a quick test through 50 independent calibration trials with the error computed in real time, which would not be possible for a conventional manual brachytherapy calibration procedure.

9. Real-time Overlay of the Template Grid on the TRUS Images

Figure 8:
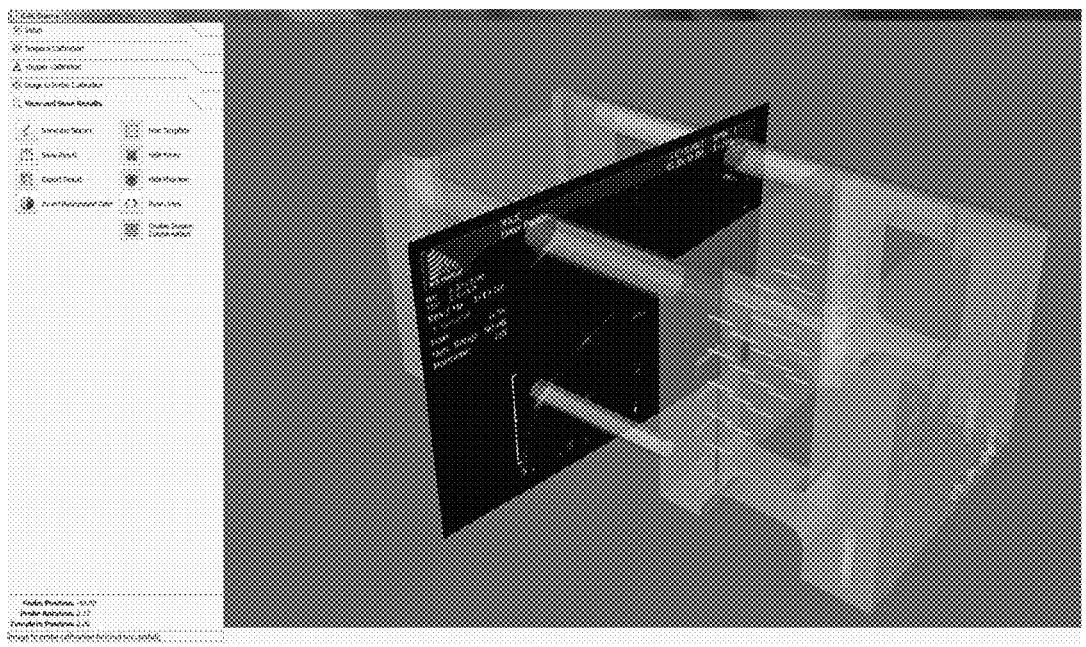
FIG. 8 is a screen shot showing an interactive graphical interface including a 3D overlay of the template grid to a TRUS image in real time, in accordance with one embodiment.

Once the calibration parameters are computed, the calibration method automatically registers (overlays) the location of the template grid onto the transverse TRUS image, and displays it to the users via an interactive 3D graphical user interface (FIG. 8). The user can rotate and enlarge the 3D scene to visually examine the spatial relationship between the TRUS image plane and the template grid. Note the matrix of dots shown in FIG. 8 are the needle guiding holes on the front surface of the template.

The calibration method also updates in real time the position change of the TRUS image and the template when the probe is being translated and/or rotated and when the template is being displaced by the user, respectively.

On newer TRUS scanners, such as the Sonix MDP or Sonix TOUCH (Ultrasonix Medical Corp.), the calibration parameters can also be set by the calibration method through a manufacturer-provided application programming interface (API) to directly update the superimposed template grid on the display of the TRUS machine.

EXAMPLE 2

To investigate the accuracy, precision, robustness, and speed of calibration method embodiments, various independent experiments were performed.

Automated Segmentation

Figure 9A:
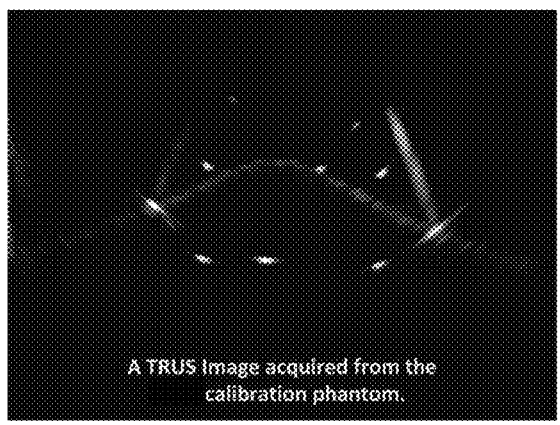
FIG. 9(a)-(b) shows screen shots demonstrating automatic segmentation of N-wires from a TRUS image in accordance with embodiments described herein: (a) a TRUS image acquired from a calibration phantom; (b) N-wire positions are correctly extracted by the automated segmentation algorithm.
Figure 9B:
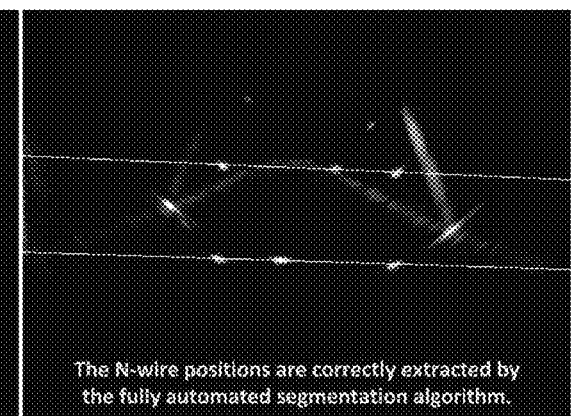

The automated segmentation algorithm of the calibration embodiment was tested with over 10,000 TRUS images acquired from the calibration phantom. These images were taken at various displacements and rotation angles to cover every possible view of the phantom N-wires. The segmentation outcomes were compared with ground truth results identified by an experienced human operator. In all the images tested, there was no failure in identifying the N-wires and a careful inspection could not identify visible segmentation errors. FIG. 9(a)-(b) shows an example of segmentation. In FIG. 9(a), a TRUS image acquired from the calibration phantom is shown, and FIG. 9(b) shows that the N-wire positions are extracted by the segmentation algorithm.

Experiments with 50 Real-time Independent Trials

This experiment was designed to validate the accuracy, reliability, and speed of the calibration method. In the experiment, the TRUS scanner used was a Sonix MDP 4.0 (Ultrasonix Medical Corp.) that operated at a central frequency of 6 MHz with an imaging depth of 7 cm. The TRUS image data was acquired digitally using Ulterius SDK provided by the manufacturer. The stepper system used was a Target Guide Stepper (Burdette Medical Systems, Inc.).

A total of 50 independent, real-time calibration trials were individually performed, with the transducer inserted and attached to the stepper at all time. In each calibration experiment:

A total of 300 live TRUS images were acquired from the calibration phantom to compute the calibration parameters. Using a calibration phantom design as in FIG. 6, two sets of N-wires were visible in a single TRUS image, the 300 images used for calibration yielded 600 data points, which is more than sufficient for the process to converge.

Another 100 live TRUS images acquired from the calibration phantom were used to compute the LRE [Eq. (4)] in order to evaluate the calibration accuracy. On each validation image, the positions of the wires #1, #3, #4, and #6 (FIG. 6) were automatically extracted and reconstructed in the 3D space using the calibration parameters. This yielded 400 LRE measurements per experiment, from which a mean and standard deviation of the errors were calculated.

This setup purposely prevented the same data from being used in both calibration and accuracy evaluation, which would create a biased validation. Finally, the LREs from all 50 independent experiments were statistically analyzed.

Table I shows validation results for the 50 independent, real-time calibration trials. LRE was computed as the "line-reconstruction error" or the "point-line distance", as defined in Eq. (4). The TRUS image had a size of 640×480 pixels and a resolution of 0.2 mm/pixel (or 5 pixels per millimeter).

TABLE I

Validation results for 50 independent, real-time calibration trials.

| Number of Trials:[a] 50 (independent) | Line Reconstruction Error (LRE: mm) |
|---|---|
| Mean (μ) | 0.57 |
| Standard deviation (σ) | 0.13 |
| Minimum (best case) | 0.26 |
| Maximum (worst case) | 0.91 |
| Runtime[b] | 20 s/trial |

[a]With a Sonix MDP scanner and a target guide stepper.
[b]Intel Q6600 2.4 GHz 4 GB-RAM Windows Server 2008 64-bit.

Key results include the following: First, all 50 calibration trials reached a sub-millimeter accuracy: the average LRE for all trials was 0.57 mm and the maximum error (the worst case scenario) was 0.91 mm. The clinical translation of this result into a brachytherapy procedure is that assuming there is no needle bending, the accuracy of needle insertion and seed placement based on the template-TRUS registration would be 0.6 mm on average.

Second, because the calculation of LRE is based on the ground-truth position of the wires #1, #3, #4, and #6 (FIG. 6) which, by the design of the calibration phantom, encompass the targeted area of the prostate in a clinical setup, the scope of the LRE provides a sound estimate of the accuracy in localizing anatomical targets in the prostate during a brachytherapy procedure.

Further, the standard deviation of the LRE was 0.13 mm, which suggests that the calibration also has excellent precision in producing a consistent and repeatable calibration. The very low variability in the calibration outcome is desirable for use in the operating room.

Finally, each of the 50 calibration trials converged in an average of 20 seconds (on an Intel Core 2 Duo Q6600 workstation at 2.4 GHz with 4 GB memory running Windows Server 2008R2 64-bit), sufficiently fast for use in the operating room.

Experiments with Different TRUS Scanners

These experiments were designed to evaluate the robustness and compatibility of calibration with ultrasound machines of different data interfaces, types/sizes, ages, and manufacturers:

Interfaces: analogue (S-video) and digital data acquisition;

Type/Size: full-size, portable and laptop size.

Ages: old and latest generations of TRUS machines were tested.

Manufacturer: TRUS scanners from four different manufacturers.

Table II lists the detailed setup for the experiments. In each experiment, 300 live TRUS images were acquired from the calibration phantom to compute the calibration parameters, and then another 100 live TRUS images to compute the LRE. To limit the testing variable to the TRUS machines only, the same Target Guide Stepper (Burdette Medical Systems, Inc., Champaign, Ill.) was used through all the experiments.

TABLE II

Experimental setup with different TRUS scanners[a]

| TRUS Scanner | Manufacturer | Data Interface | Type | Age |
|---|---|---|---|---|
| Leopard 2001 | BK-Medical Systems, Inc., Peabody, MA | S-video | Full | 1980s |
| Sonix MDP 4.0 | Ultrasonix Medical Corp., Burnaby, BC, Canada | S-video | Full | 2000s |
| Sonix TOUCH (analogue) | Ultrasonix Medical Corp., Burnaby, BC, Canada | S-video | Full | 2010s |
| Sonix TOUCH (digital) | Ultrasonix Medical Corp., Burnaby, BC, Canada | Ulterius Digital | Full | 2010s |
| Terason 2000 | Teratech Corp., Burlington, MA | S-video | Laptop | 2000s |
| VLCUS | Carolina Medical Systems, Inc., NC | S-video | Portable | 1990s |

[a]Stepper used: Target Guide Stepper (Burdette Medical Systems).

Table III shows the validation results.

TABLE III

Validation results with different TRUS scanners[a]

| TRUS Scanner | LRE: mm Mean | LRE: mm Std | Frequency (MHz) | Depth (cm) | Data Interface | Type | Age |
|---|---|---|---|---|---|---|---|
| Leopard 2001 | 0.37 | 0.23 | 6.5 | 9.0 | S-video | Fun | 1990s |
| Sonix MDP 4.0 | 0.38 | 0.24 | 6.0 | 7.0 | S-video | Full | 2000s |
| Sonix TOUCH (analogue) | 0.33 | 0.25 | 6.0 | 7.0 | S-video | Full | 2010s |
| Sonix TOUCH (digital) | 0.37 | 0.27 | 6.0 | 7.0 | Ulterius Digital | Full | 2010s |
| Terason 2000 | 0.35 | 0.26 | Norm | 8.0 | S-video | Laptop | 2000s |
| VLCUS | 0.41 | 0.26 | Norm | 7.0 | S-video | Portable | 1990s |
| Average | 0.37 | 0.25 | — | — | — | — | — |

[a]All tests used the same Target Guide Stepper (Burdette Medical Systems).

Key observations and results include the following: First, the calibration was able to consistently achieve submillimeter, high calibration accuracy and precision across all the tested TRUS imaging platforms: the average LRE was 0.37 mm with a standard deviation of 0.25 mm. There was no difference in accuracy between the digital data acquisition (Sonix TOUCH Ulterius API) and the analogue data acquisition from Svideo (the rest of the tested scanners), even though the digital platform offers better image quality (less noise) and finer per-pixel resolution than the analogue units. In the tests, the digital TRUS image had 0.2 mm/pixel resolution (or 5 pixels per millimeter) while the analogue image had only 0.26 mm/pixel resolution (or 3.8 pixels per millimeter). This suggests that the calibration method does not demand high image quality and resolution to perform accurately, and would be compatible with the majority of TRUS machines currently available which are equipped with a standard analogue data output.

There was also no difference in accuracy between the latest TRUS machines (manufactured after 2000) and some of the older ones (manufactured in the 1990s). The newer TRUS scanners typically offer more polished hardware design and better signal transmission, retrieving, and processing quality, which in turn results in overall better TRUS imaging quality than the older technologies. This result confirms the robustness the calibration in dealing with varying TRUS hardware and imaging conditions.

Finally, the calibration achieved the same level of accuracy in different types of TRUS machines including standard full-size, portable and even laptop-size TRUS scanners. This suggests that the calibration does not require high-processing power from a typical full-scale TRUS system to function properly, which provides more flexibility and mobility in an intraoperative brachytherapy situation to work with small, portable TRUS devices if desired.

Experiments with Different Brachytherapy Stepper Systems

These experiments were designed to examine the robustness and compatibility of the calibration embodiment with different brachytherapy stepper systems, offering varying position tracking quality. The experiments included four different Target Guide Steppers and an Accuseed DS300 Stepper. In each experiment, 300 live TRUS images were acquired from the calibration phantom to compute the calibration parameters, and then another 100 live TRUS images to compute the LRE. Table IV gives the details of the tested stepper systems. To limit the testing variable to the stepper systems only, we used the digital data acquisition from Sonix TOUCH (Ultrasonix Medical Corp.) for all experiments.

TABLE IV

Experimental setup with different brachytherapy stepper systems

| Brachytherapy stepper | Manufacturer | Number of Units Tested |
|---|---|---|
| Target guide stepper | Burdette Medical Systems, Inc., Champaign, IL | 4 |
| Accuseed DS300 Stepper | Computerized Medical Systems, Inc., Saint Louis, MO | 1 |

Table V shows the validation results with different brachytherapy stepper systems.

TABLE V

Validation results with different brachytherapy stepper systems[a]

| Brachytherapy | LRE: mm | | |
|---|---|---|---|
| Stepper | Mean | Std | Manufacturer |
| Target guide #1 | 0.25 | 0.16 | Burdette Medical Systems, Inc., Champaign, IL |
| Target guide #2 | 0.34 | 0.21 | |
| Target guide #3 | 0.33 | 0.25 | |
| Target guide #4 | 0.36 | 0.10 | |
| Target guide stepper (average) | 0.32 | 0.18 | |
| Accuseed DS 300 | 0.16 | 0.10 | Computerized Medical Systems, Inc., Saint Louis, MO |

[a]TRUS images acquired by Sonix TOUCH Analogue (Ultrasonix Corp.).

Key observations and findings include the following: The calibration embodiment consistently achieved sub-millimeter, high calibration accuracy and precision across all the tested brachytherapy stepper systems: LREs of all tests were below 0.5 mm with an average of 0.29 mm and a standard deviation of 0.16 mm. This suggests that the calibration is robust in working with different stepper systems of varying mechanical condition and/or tracking quality.

For the four Target Guide Steppers (Burdette Medical Systems, Inc., Champaign, Ill.) tested, the mean of LRE was 0.32 mm with a standard deviation of 0.18 mm. This is consistent with the results of the tests with multiple TRUS scanners using a Target-Guide Stepper (Table III).

More importantly, we found that the Accuseed DS 300 achieved a significantly higher calibration accuracy and precision than Target Guide steppers: the LRE mean of the Accuseed was one-half that of the Target Guides (0.16 mm versus 0.32 mm), with a much smaller standard deviation as well (0.10 mm versus 0.18 mm). This result is due to the fact that the Accuseed DS 300 stepper provides higher position tracking accuracy than the Target Guide stepper and is also mechanically more stable and precise in design.

There are two significant clinical implications of these findings. First, any improvement in the stepper tracking accuracy and precision, and the mechanical stability, may significantly improve the brachytherapy calibration. Second, the calibration method is capable of providing real-time quality assurance of the brachytherapy stepper systems in the operating room, by monitoring and reporting any unexpected change in the calibration accuracy and precision in an intraoperative brachytherapy procedure.

Experiments with Needle Insertion to Validate Template-TRUS Calibration

The template-to-TRUS calibration/registration outcome was evaluated by measuring a target registration error (TRE) with the water tank method (Goldstein et al., 2002; Mutic et al., 2000). Seven brachytherapy needles were inserted to the same depth through the template holes C3, C5, D5, E3, E5, b4, and e4 and scanned by TRUS in a water tank. The brachytherapy needles used in the tests were 18-gauge Mick TP Prostate Seeding Needles (Mick Radio-Nuclear Instruments, Inc., Bronx, N.Y.), having a 1.270±0.013 mm outer diameter. The TRUS image had a size of 640×480 pixels and a resolution of 0.2 mm/pixel (or 5 pixels per millimeter). The position of each needle tip in the TRUS image was manually segmented by an experienced human operator and then compared to the computed location by iCAL to obtain the respective TRE value.

Table VI shows the TRE results of the template-TRUS calibration accuracy.

TABLE VI

TRE results of needle insertion to validate template-TRUS calibration accuracy

| | Template grid | | | | | | | | |
|---|---|---|---|---|---|---|---|---|---|
| | C3 | C5 | D5 | E3 | E5 | b4 | e4 | Mean | Std |
| TRE (mm) | 0.31 | 0.25 | 0.91 | 0.56 | 0.88 | 0.35 | 0.69 | 0.56 | 0.27 |

Key observations and findings include the following. The TREs were all below 1 mm in the seven needle insertion experiments, with an average of 0.56 mm and a standard deviation of 0.27 mm. These results suggest excellent template-TRUS calibration accuracy and precision. Further, the TRE measurements are consistent with the sub-millimeter LRE results reported in Tables I, III, and V.

The tested locations where the needles were inserted (C3, C5, D5, E3, E5, b4, and e4) encompassed the targeted area of the prostate in a clinical setup. Therefore the TRE measured in this setup provides a good approximation of the template-TRUS calibration accuracy using the calibration method in the operating room.

Figure 10:
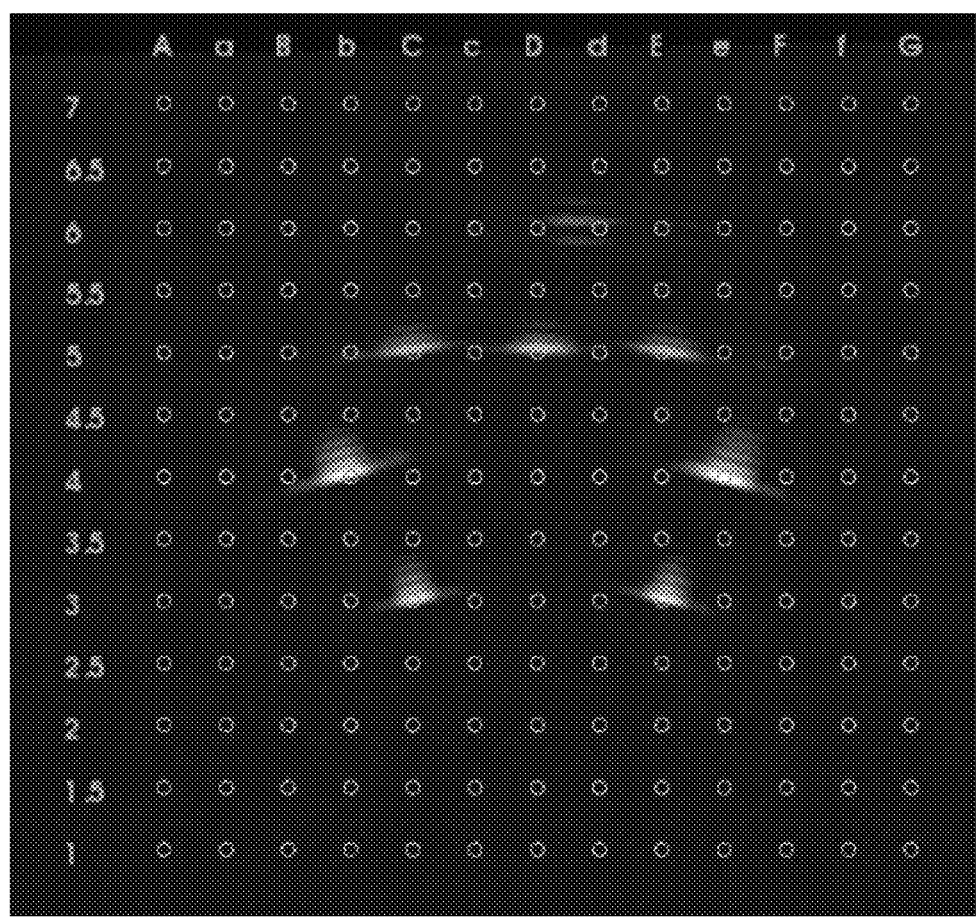
FIG. 10 is a screen shot showing brachytherapy needle insertion to validate template-TRUS calibration accuracy.

FIG. 10 shows a visual confirmation of the results: the template grid was registered to the TRUS images and displayed to the user in real time while the needles were being inserted through the grid holes in the water tank. As can be clearly observed, the needle artifacts in the TRUS image, which were the corresponding positions of the needle tip inserted through grid holes C5, D5, E5, b4, e4, C3, and E3, all perfectly coincided with the computed template grid positions, showing excellent TRE.

3D Overlay of Template to TRUS

A 3D overlay of the template grids on the real-time TRUS images, after the calibration parameters were computed, was viewed on a display screen. The grid matrix in the view was the front, painted face of the template and the rear gray-scale image was the real-time TRUS images (which showed the N-wires of the calibration phantom). The user was able to interact with the 3D display to translate, rotate, and zoom in/out the 3D overlay with various viewing angles and positions (e.g., front, left, right, and top).

Because the positions of both the TRUS probe and the template were tracked in real-time by the stepper (and monitored by the calibration embodiment), the calibration accurately updated and displayed any position change of the TRUS image and the template grids while the user translated or rotated the TRUS transducer during the scan, or displaced the template back or forth.

The contents of all cited publications are incorporated herein by reference in their entirety.

Equivalents

Those skilled in the art will recognize or be able to ascertain variants of the embodiments described herein. Such variants are within the scope of the invention and are covered by the appended claims.

REFERENCES

Boctor, E. M., I. Iordachita, G. Fichtinger, and G. D. Hager, "Ultrasound selfcalibration," Proceedings of SPIE Medical Imaging: Visualization, Image-Guided Procedures, and Display, edited by K. R. Cleary and R. L. Galloway, Jr. (SPIE, San Diego, Calif., 2006), Vol. 6141, pp. 61412N1-61412N12.

Boctor, E. M., I. Iordachita, G. Fichtinger, and G. D. Hager, "Real-time quality control of tracked ultrasound," Lect. Notes Comput. Sci. 3749,621-630 (2005).

Chen, T. K., A. D. Thurston, R. E. Ellis, and P. Abolmaesumi, "A real-time freehand ultrasound calibration system with automatic accuracy feedback and control," Ultrasound Med. Biol. 35(1), 79-93 (2009).

Goldstein, A., M. Yudelev, R. K. Sharma, and E. Arterbery, "Design of quality assurance for sonographic prostate brachytherapy needle guides," J. Ultrasound Med. 21,947-954 (2002).

Mutic, S., D. A. Low, G. H. Nussbaum, J. F. Williamson, and D. Haefner, "A simple technique for alignment of perineal needle template to ultrasound image grid for permanent prostate implants," Med. Phys. 27, 141-143 (2000).

Ng, A., A. Beiki-Ardakan, S. Tong, D. Moseley, J. Siewerdsen, D. Jaffray, and I. W. T. Yeung, "A dual modality phantom for cone beam CT and ultrasound image fusion in prostate implant," Med. Phys. 35, 2062-2071 (2008).

The invention claimed is:

1. An ultrasound calibration phantom, comprising: a first fiducial structure having a selected geometric arrangement corresponding to a transverse plane and a second fiducial structure corresponding to a sagittal image plane; a portion configured to mechanically couple the ultrasound calibration phantom to a trans rectal ultrasound (TRUS) stepper; and a guide for at least one surgical instrument; wherein the first fiducial structure, the second fiducial structure, and the guide are mechanically coupled together in a unibody structure; wherein the first fiducial structure, the second fiducial structure, and the guide are disposed at a selected relative pose in a three dimensional space.

2. The ultrasound calibration phantom of claim 1, further comprising an ultrasound coupling medium.

3. The ultrasound calibration phantom of claim 1, further comprising a portion that interfaces with an ultrasound probe.

4. The ultrasound calibration phantom of claim 3, wherein the ultrasound probe is a TRUS probe.

5. The ultrasound calibration phantom of claim 1, wherein the first fiducial structure comprises a plurality of fiducial lines in a selected geometric arrangement; and the second fiducial structure comprises a plurality of fiducial lines in a selected geometric arrangement.

6. The ultrasound calibration phantom of claim 5 wherein at least one of the first fiducial structure and the second fiducial structure comprises at least one Z-wire structure.

7. The ultrasound calibration phantom of claim 1, wherein the guide comprises a template.

8. The ultrasound calibration phantom of claim 1, wherein the guide comprises a brachytherapy template.

9. The ultrasound calibration phantom of claim 8, wherein the guide comprises a brachytherapy needle template.

10. The ultrasound calibration phantom of claim 9, wherein the guide comprises a prostate brachytherapy needle template.

11. The ultrasound calibration phantom of claim 1, wherein the guide comprises a stepper.

12. A method for calibrating an ultrasound system, comprising:
continuously acquiring ultrasound images from an ultrasound calibration phantom including at least one fiducial structure having a selected geometric arrangement while simultaneously tracking motion of an ultrasound probe;
performing a temporal calibration to synchronize individual ultrasound image frames with their respective positions;
segmenting the ultrasound images of the ultrasound calibration phantom to extract pixel locations of phantom geometry;
subjecting the pixel locations of the segmented phantom geometry, together with their corresponding physical coordinates in the ultrasound calibration phantom, to a closed-form formula or an iterative solver to calculate calibration parameters;
determining accuracy of a calibration result, measured as a reconstruction error against a known ground truth; and
exporting a final calibration outcome.

13. The method of claim 12, wherein determining accuracy of the calibration result includes determining whether the calibration result is satisfactory.

14. The method of claim 13, wherein determining accuracy of the calibration result includes updating and displaying reconstruction error in real time.

15. The method of claim 14, including exporting a final calibration outcome when the determining is completed or when the reconstruction error reaches an acceptable level.

16. The method of claim 12, wherein the motion of the ultrasound probe includes translation and/or rotation.

17. The method of claim 12, including using the method for real-time monitoring of ultrasound images during a clinical procedure.

18. The method of claim 17, wherein the clinical procedure is a brachytherapy procedure.

19. The method of claim 17, wherein the clinical procedure is a TRUS brachytherapy procedure.

20. The method of claim 12, wherein the ultrasound system is a TRUS system and the ultrasound probe is a TRUS probe.

* * * * *